United States Patent
Haubrich et al.

(10) Patent No.: US 8,497,804 B2
(45) Date of Patent: Jul. 30, 2013

(54) HIGH DIELECTRIC SUBSTRATE ANTENNA FOR IMPLANTABLE MINIATURIZED WIRELESS COMMUNICATIONS AND METHOD FOR FORMING THE SAME

(75) Inventors: Gregory J. Haubrich, Champlin, MN (US); Joyce K. Yamamoto, Maple Grove, MN (US); Duane N. Mateychuk, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 1248 days.

(21) Appl. No.: 12/347,379

(22) Filed: Dec. 31, 2008

(65) Prior Publication Data

US 2010/0109958 A1   May 6, 2010

Related U.S. Application Data

(60) Provisional application No. 61/110,542, filed on Oct. 31, 2008.

(51) Int. Cl.
 *H01Q 1/38* (2006.01)
(52) U.S. Cl.
 USPC .................................. 343/700 MS; 607/60
(58) Field of Classification Search
 USPC ............... 343/700 MS, 909; 607/60; 600/302
 See application file for complete search history.

(56) References Cited

U.S. PATENT DOCUMENTS

| | | | |
|---|---|---|---|
| 5,023,624 A | 6/1991 | Heckaman et al. | |
| 5,198,924 A | 3/1993 | Jansson | |
| 5,219,377 A | 6/1993 | Poradish | |
| 5,387,888 A | 2/1995 | Eda et al. | |
| 5,620,476 A | 4/1997 | Truex et al. | |
| 5,861,019 A | 1/1999 | Sun et al. | |
| 6,107,227 A | 8/2000 | Jacquin et al. | |
| 6,320,547 B1 | 11/2001 | Fathy et al. | |
| 6,391,082 B1 | 5/2002 | Holl | |

(Continued)

FOREIGN PATENT DOCUMENTS

| | | |
|---|---|---|
| EP | 1362614 A1 | 11/2003 |
| WO | 0102468 A1 | 1/2001 |
| WO | 2006039699 A2 | 4/2006 |
| WO | 2009079349 | 6/2009 |

OTHER PUBLICATIONS

Caiazzo, et al., A Metamaterial Surface for Compact Cavity Resonators, IEEE AP Letters, 2004, pp. 261-264, vol. 3.

(Continued)

*Primary Examiner* — Hoanganh Le
(74) *Attorney, Agent, or Firm* — Stephen W. Bauer; Michael J. Ostrom (57) ABSTRACT

An antenna structure for an implantable medical device (IMD) is provided including a lower dielectric biocompatible antenna portion positioned on a body side of the structure and a high dielectric portion including at least one dielectric substrate having a high dielectric constant positioned on a device side of the structure. The biocompatible antenna portion is derived from an antenna layer, a biocompatible surface layer, and at least one layer of biocompatible dielectric material (e.g., high temperature cofire ceramic (HTCC) material) that provides a matching gradient between the antenna and the surrounding environment. The high dielectric portion may include at least one layer of low temperature cofire ceramic (LTCC) material. The high dielectric portion may be bonded to the biocompatible antenna portion or cofired with the biocompatible antenna portion to form a single bilayer monolithic antenna structure having a lower dielectric HTCC biocompatible antenna portion and a high dielectric LTCC portion.

11 Claims, 5 Drawing Sheets

U.S. PATENT DOCUMENTS

| | | | |
|---|---|---|---|
| 6,414,835 | B1 | 7/2002 | Wolf et al. |
| 6,556,169 | B1 | 4/2003 | Fukuura et al. |
| 6,580,402 | B2 | 6/2003 | Navarro et al. |
| 7,012,327 | B2 | 3/2006 | Huff et al. |
| 7,122,891 | B2 | 10/2006 | Dishongh et al. |
| 7,164,572 | B1 | 1/2007 | Burdon et al. |
| 7,289,063 | B2 | 10/2007 | Zaghloul |
| 7,317,946 | B2 | 1/2008 | Twetan et al. |
| 7,392,015 | B1 | 6/2008 | Farlow et al. |
| 7,796,043 | B2 * | 9/2010 | Euliano et al. ............ 340/573.1 |
| 2004/0189528 | A1 | 9/2004 | Killen et al. |
| 2005/0134520 | A1 | 6/2005 | Rawat et al. |
| 2005/0203584 | A1 | 9/2005 | Twetan et al. |
| 2006/0017651 | A1 | 1/2006 | Werner et al. |
| 2006/0092079 | A1 | 5/2006 | de Rochemont |
| 2006/0212096 | A1 | 9/2006 | Stevenson |
| 2006/0214855 | A1 | 9/2006 | Harada et al. |
| 2006/0247712 | A1 | 11/2006 | Fuller et al. |
| 2007/0060970 | A1 | 3/2007 | Burdon et al. |
| 2007/0200706 | A1 | 8/2007 | Lee |
| 2007/0236861 | A1 | 10/2007 | Burdon et al. |
| 2008/0021522 | A1 | 1/2008 | Verhoef et al. |
| 2009/0046028 | A1 | 2/2009 | Han et al. |
| 2009/0149918 | A1 * | 6/2009 | Krulevitch et al. ............ 607/60 |
| 2010/0109966 | A1 | 5/2010 | Mateychuk et al. |
| 2011/0009925 | A1 * | 1/2011 | Leigh et al. .................... 607/60 |

OTHER PUBLICATIONS

Wu, et al., A study Using Metamaterials As Antenna Substrate to Enhance Gain, Pier 51, 2005, pp. 295-328.

Mosallaei, et al, Antenna Miniaturization and Bandwidth Enhancement Using a Reactive Impedance Substrate, IEEE APS, Sep. 2004, pp. 2403-2414, vol. 52 No. 9.

Broas, et al., A High Impedance Ground Plane Applied to a Cellphone Handset Geometry, IEEE MTT, Jul. 2001, pp. 1262-1265, vol. 49 No. 7.

Lal C. Godara, Application of Antenna Arrays to Mobile Communications, Part I: Performance Improvement, Feasibility, and System Considerations, Proceedings of the IEEE, Jul. 1997, pp. 1031-1060, vol. 85, No. 7.

Lal C. Godara, Application of Antenna Arrays to Mobile Communications, Part II: Beam-Forming and Direction-of-Arrival Considerations, Proceedings of the IEEE, Aug. 1997, pp. 1195-1245, vol. 85, No. 8.

(PCT US2009/061410) PCT Notification of Transmittal of the International Search Report and the Written Opinion of the International Searching Authority, 11 pages.

Dr. Lawrence Williams et al., "Enhance the Design of LTCC RF Modules, Microwaves & FR," Sep. 2003, pp. 90-96, 120.

* cited by examiner

HIGH DIELECTRIC SUBSTRATE ANTENNA FOR IMPLANTABLE MINIATURIZED WIRELESS COMMUNICATIONS AND METHOD FOR FORMING THE SAME

RELATED APPLICATION

This application claims the benefit of and priority to U.S. Provisional Application Ser. No. 61/110,542, filed Oct. 31, 2008, entitled, "High Dielectric Substrate Antenna for Implantable Miniaturized Wireless Communications and Method for Forming the Same," the contents of which are incorporated by reference herein in its entirety.

TECHNICAL FIELD

The present invention relates generally to implantable medical devices (IMDs) and, more particularly, the present invention relates to telemetry antennas suitable for deployment in IMDs.

BACKGROUND

Various types of devices have been developed for implantation into the human body to provide various types of health-related therapies, diagnostics and/or monitoring. Examples of such devices, generally known as implantable medical devices (IMDs), include cardiac pacemakers, cardioverter/defibrillators, cardiomyostimulators, cardiac event monitors, various physiological stimulators including nerve, muscle, and deep brain stimulators, various types of physiological monitors and sensors, and drug delivery systems, just to name a few. IMDs typically include functional components contained within a hermetically sealed enclosure or housing, which is sometimes referred to as a "can." In some IMDs, a connector header or connector block is attached to the housing, and the connector block facilitates interconnection with one or more elongated electrical medical leads. The header block is typically molded from a relatively hard, dielectric non-conductive polymer. The header block includes a mounting surface that conforms to, and is mechanically affixed against, a mating sidewall surface of the housing.

It has become common to provide a communication link between the hermetically sealed electronic circuitry of the IMD and an external programmer, monitor, or other external medical device ("EMD") in order to provide for downlink telemetry transmission of commands from the EMD to the IMD and to allow for uplink telemetry transmission of stored information and/or sensed physiological parameters from the IMD to the EMD. Conventionally, the communication link between the IMD and the EMD is realized by encoded radio frequency ("RF") transmissions between an IMD telemetry antenna and transceiver and an EMD telemetry antenna and transceiver. Generally, the IMD antenna is disposed within the hermetically sealed housing; however, the typically conductive housing adversely attenuates the radiated RF field and limits the data transfer distance between the programmer head and the IMD RF telemetry antennas to a few inches. This type of system may be referred to as a "near field" telemetry system. In order to provide for "far field" telemetry, or telemetry over distances of a few to many meters from an IMD or even greater distances, attempts have been made to provide antennas outside of the hermetically sealed housing and within the header block. Many of such attempts of positioning an RF telemetry antenna outside of the hermetically sealed housing and in the header block have utilized wire antennas or planar, serpentine antennas, such as the antennas described in U.S. Pat. No. 7,317,946, which is hereby incorporated by reference in its entirety. The volume associated with the antenna and header block conventionally required for the implementation of distance telemetry in implanted therapy and diagnostic devices has been a significant contributor to the size of the IMD.

SUMMARY

In one or more embodiments, a high dielectric substrate is provided in an antenna structure for an implantable medical device (IMD) for providing isolation between an antenna positioned within the antenna structure and the IMD in order to allow for miniaturization of the antenna structure. The antenna structure includes a biocompatible antenna portion positioned on a body side of the antenna structure having an effective lower dielectric constant than the dielectric constant of the high dielectric substrate, where the high dielectric substrate is included within high dielectric portion having an effective high dielectric constant positioned on a device side of the antenna structure.

In one or more embodiments, the biocompatible antenna portion of the antenna structure is derived from a plurality of layers of material including the material forming the antenna and a biocompatible surface layer. The biocompatible surface layer is positioned as the outermost layer of the antenna structure serving as an interface for the antenna structure to the surrounding environment (i.e., the body in which the IMD is implanted). In some embodiments, the biocompatible body side portion may include electrodes and routing circuitry that provide a connection between the antenna and other components, such as to MD circuitry components. In some embodiments, the plurality of layers in the biocompatible antenna portion include a plurality of layers of high temperature cofire ceramic (HTCC) material, where all of the layers of materials forming the biocompatible antenna portion may be cofired together to form a monolithic structure. In some embodiments, the biocompatible antenna portion possesses a dielectric constant that provides matching between the antenna and the surrounding environment to mitigate energy reflection effects at the transition from the antenna structure to the surrounding environment.

In one or more embodiments, the high dielectric portion is bonded or otherwise connected to the biocompatible antenna portion while establishing an electrical connection between the high dielectric portion and the biocompatible antenna portion. In some embodiments, the biocompatible antenna portion is joined to the high dielectric portion to bond the two portions together and provide electrical continuity between the two portions. In some embodiments, the high dielectric portion includes a plurality of layers of low temperature cofire ceramic (LTCC) material that enables the incorporation of high dielectric constant materials that are cofired together with the biocompatible antenna portion to form a single bilayer monolithic antenna structure having an upper, body-side, lower dielectric HTCC biocompatible antenna portion and a lower device-side, high dielectric LTCC portion. By using cofired technologies to form the high dielectric portion and the biocompatible antenna portion, component miniaturization advances can be achieved to significantly reduce the size of the antenna structure used for IMD wireless communications.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The following detailed description is merely illustrative and is not intended to limit the invention or the application and uses of the invention. Furthermore, there is no intention to be bound by any expressed or implied theory presented in the preceding technical field, background, brief summary or the following detailed description.

The following description refers to components or features being "connected" or "coupled" together. As used herein, unless expressly stated otherwise, "connected" means that one component/feature is directly or indirectly connected to another component/feature, and not necessarily mechanically. Likewise, unless expressly stated otherwise, "coupled" means that one component/feature is directly or indirectly coupled to another component/feature, and not necessarily mechanically. Thus, although the figures may depict example arrangements of elements, additional intervening elements, devices, features, or components may be present in an actual embodiment (assuming that the functionality of the IMDs are not adversely affected).

In one or more embodiments, an IMD having a monolithic antenna structure derived from a plurality of discrete dielectric layers is provided. For the sake of brevity, conventional techniques and aspects related to RF antenna design, IMD telemetry, RF data transmission, signaling, IMD operation, connectors for IMD leads, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

An IMD antenna generally has two functions: to convert the electromagnetic power of a downlink telemetry transmission of an EMD telemetry antenna propagated through the atmosphere (and then through body tissues) into a signal (e.g., a UHF signal or the like) that can be processed by the IMD transceiver into commands and data that are intelligible to the IMD electronic operating system; and to convert the uplink telemetry signals (e.g., a UHF signal or the like) of the IMD transceiver electronics into electromagnetic power propagated through the body tissue and the atmosphere so that the EMD telemetry antenna or antennas can receive the signals.

Figure 1:
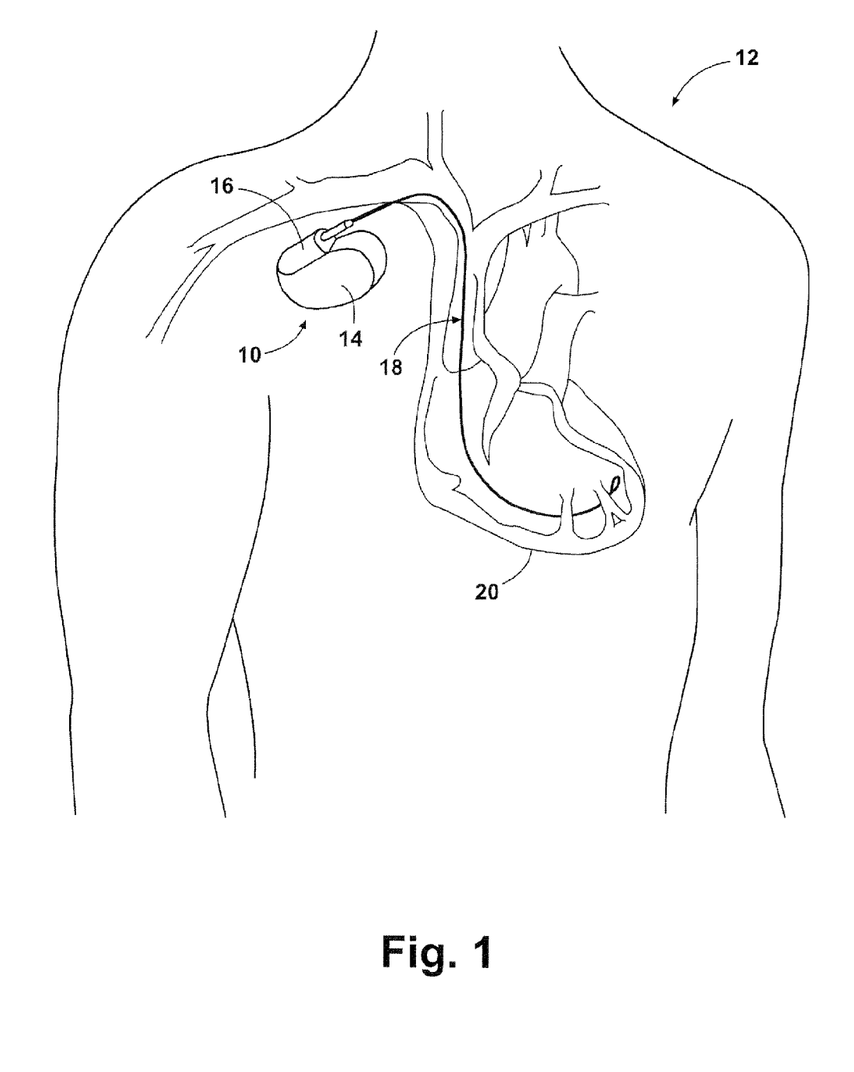
FIG. 1 illustrates an implantable medical device implanted in a human body in accordance with one or more embodiments of the present disclosure.

FIG. 1 is a perspective view of an IMD 10 implanted within a human body 12 in which one or more embodiments of the invention may be implemented. IMD 10 comprises a hermetically sealed housing 14 (or "can") and connector header or block module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions in a manner well known in the art. For example, such leads may enter at an end of header block 16 and be physically and electrically connected to conductive receptacles, terminals, or other conductive features located within header block 16. IMD 10 may be adapted to be implanted subcutaneously in the body of a patient such that it becomes encased within body tissue and fluids, which may include epidermal layers, subcutaneous fat layers, and/or muscle layers. While IMD 10 is depicted in FIG. 1 in an ICD configuration, it is understood that this is for purposes of illustration only and IMD 10 may comprise any type of medical device requiring a telemetry antenna.

In some embodiments, hermetically sealed housing 14 is generally circular, elliptical, prismatic, or rectilinear, with substantially planar major sides joined by perimeter sidewalls. Housing 14 is typically formed from pieces of a thin-walled biocompatible metal such as titanium. Two half sections of housing 12 may be laser seam welded together using conventional techniques to form a seam extending around the perimeter sidewalls. Housing 14 and header block 16 are often manufactured as two separate assemblies that are subsequently physically and electrically coupled together. Housing 14 may contain a number of functional elements, components, and features, including (without limitation): a battery; a high voltage output capacitor; integrated circuit ("IC") devices; a processor; memory elements; a therapy module or circuitry; an RF module or circuitry; and an antenna matching circuit. These components may be assembled in spacers and disposed within the interior cavity of housing 14 prior to seam welding of the housing halves. During the manufacturing process, electrical connections are established between components located within housing 14 and elements located within header block 16. For example, housing 14 and header block 16 may be suitably configured with IC connector pads, terminals, feedthrough elements, and other features for establishing electrical connections between the internal therapy module and the therapy lead connectors within header block 16 and for establishing connections between the internal RF module and a portion of a telemetry antenna located within header block 16. Structures and techniques for establishing such electrical (and physical) feedthrough connections are known to those skilled in the art and, therefore, will not be described in detail herein. For example, U.S. Pat. No. 6,414,835 describes a capacitive filtered feedthrough array for an implantable medical device, the contents of which are hereby incorporated by reference.

Header block 16 is preferably formed from a suitable dielectric material, such as a biocompatible synthetic polymer. In some embodiments, the dielectric material of header block 16 may be selected to enable the passage of RF energy that is either radiated or received by a telemetry antenna (not shown in FIG. 1) encapsulated within header block 16. The specific material for header block 16 may be chosen in response to the intended application of IMD 10, the electrical characteristics of the environment surrounding the implant location, the desired operating frequency range, the desired RF antenna range, and other practical considerations.

Figure 2:
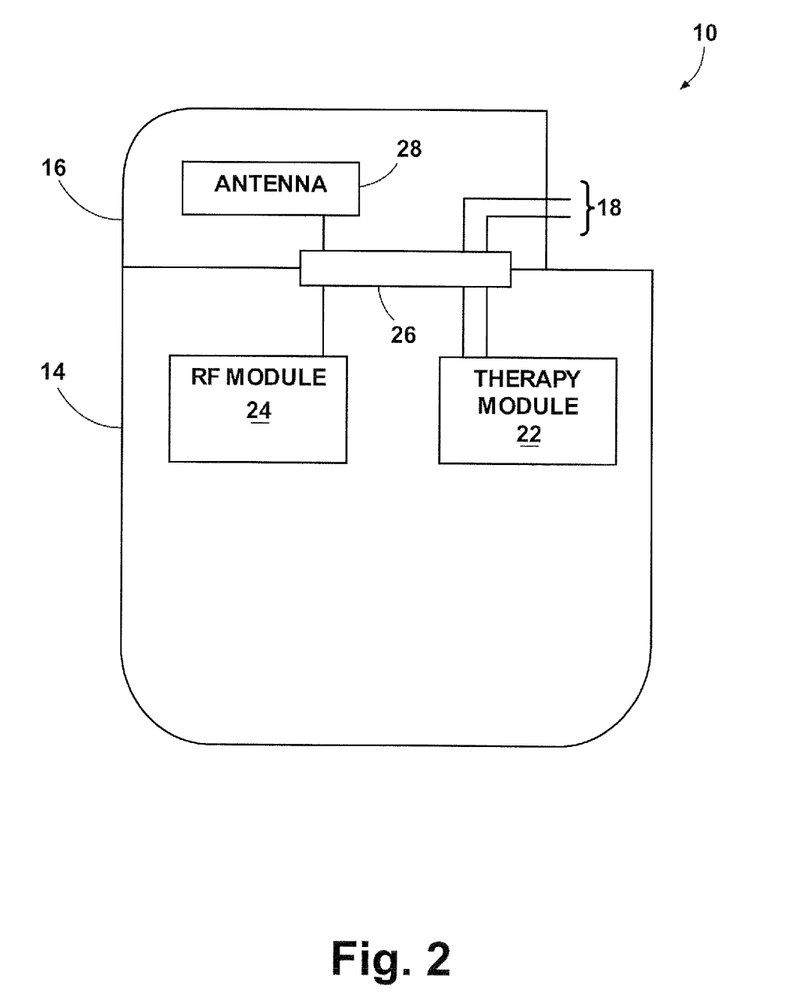
FIG. 2 is a schematic block diagram illustration of exemplary implantable medical device in accordance with one or more embodiments of the present disclosure.

FIG. 2 is a simplified schematic representation of an IMD 10 and several functional elements associated therewith. IMD 10 generally includes hermetically sealed housing 14 and header block 16 coupled to housing 14, a therapy module 22 contained within housing 14, and an RF module 24 contained within housing 14. In practice, IMD 10 will also include a number of conventional components and features necessary to support the functionality of IMD 10 as known in the art. Such conventional elements will not be described herein.

Therapy module 22 may include any number of components, including, without limitation: electrical devices, ICs, microprocessors, controllers, memories, power supplies, and the like. Briefly, therapy module 22 is configured to provide the desired functionality associated with the IMD 10, e.g., defibrillation pulses, pacing stimulation, patient monitoring, or the like. In this regard, therapy module 22 may be coupled to one or more sensing or therapy leads 18. In practice, the connection ends of therapy leads 18 are inserted into header block 16, where they establish electrical contact with conductive elements coupled to therapy module 22. Therapy leads 18 may be inserted into suitably configured lead bores formed within header block 16. In the example embodiment, IMD 10 includes a feedthrough element 26 that bridges the transition between housing 14 and header block 16. Therapy leads 18 extend from header block 16 for routing and placement within the patient.

RF module 24 may include any number of components, including, without limitation: electrical devices, ICs, amplifiers, signal generators, a receiver and a transmitter (or a transceiver), modulators, microprocessors, controllers, memories, power supplies, and the like. RF module 24 may further include a matching circuit or a matching circuit may be positioned between RF module 24 and antenna 28. Matching circuit may include any number of components, including, without limitation: electrical components such as capacitors, resistors, or inductors; filters; baluns; tuning elements; varactors; limiter diodes; or the like, that are all suitably configured to provide impedance matching between antenna 28 and RF module 24, thus improving the efficiency of antenna 28. Briefly, RF module 24 supports RF telemetry communication for IMD 10, including, without limitation: generating RF transmit energy; providing RF transmit signals to antenna 28; processing RF telemetry signals received by antenna 28, and the like. In practice, RF module 24 may be designed to leverage the conductive material used for housing 14 as an RF ground plane (for some applications), and RF module 24 may be designed in accordance with the intended application of IMD 10, the electrical characteristics of the environment surrounding the implant location, the desired operating frequency range, the desired RF antenna range, and other practical considerations.

Antenna 28 is coupled to RF module 24 to facilitate RF telemetry between IMD 10 and an EMD (not shown). Generally, antenna 28 is suitably configured for RF operation (e.g., UHF or VHF operation, 401 to 406 MHz for the MICS/MEDS bands, and/or 900 MHz/2.4 GHz, and/or other ISM bands, etc.). In the example embodiment shown in FIG. 2, antenna 28 is located within header block 16 and outside of housing 14. However, the volume associated with the antenna 28 and the volume within the header block 16 required for the implementation of distance telemetry in implanted therapy and diagnostic devices can be a significant contributor to the size of the IMD 10. Thus, in one or more embodiments, antenna 28 may be formed having a reduced size and without requiring the volume associated header block 16. Antenna 28 may have characteristics resembling a monopole antenna, characteristics resembling a dipole antenna, characteristics resembling a coplanar waveguide antenna, characteristics resembling a slot antenna, characteristics resembling a patch antenna, and/or characteristics resembling a transmission line antenna. Antenna 28 may also have any number of radiating elements, which may be driven by any number of distinct RF signal sources. In this regard, antenna 28 may have a plurality of radiating elements configured to provide spatial or polarization diversity In one or more embodiments, antenna 28 is coupled to RF module 24 via an RF feedthrough in feedthrough 26, which bridges housing 14 and header block 16. Antenna 28 may include a connection end that is coupled to RF feedthrough in feedthrough 26 via a conductive terminal or feature located within header block 16. Briefly, a practical feedthrough 26 includes a ferrule supporting a non-conductive glass or ceramic insulator. The insulator supports and electrically isolates a feedthrough pin from the ferrule. During assembly of housing 14, the ferrule is welded to a suitably sized hole or opening formed in housing 14. RF module 24 is then electrically connected to the inner end of the feedthrough pin. The connection to the inner end of the feedthrough pin can be made by welding the inner end to a substrate pad, or by clipping the inner end to a cable or flex wire connector that extends to a substrate pad or connector. The outer end of the feedthrough pin serves as a connection point for antenna 28, or as a connection point for an internal connection socket, terminal, or feature that receives the connection end of antenna 28. The feedthrough 26 for antenna 28 may be located on any desired portion of housing 14 suitable for a particular design. In some embodiments, RF module 24 may be located externally from housing 14 (e.g., such as in a cavity formed on the exterior of housing 14 or any external location) with connections to antenna 28 that are not required to pass through feedthrough 26.

Figure 3:
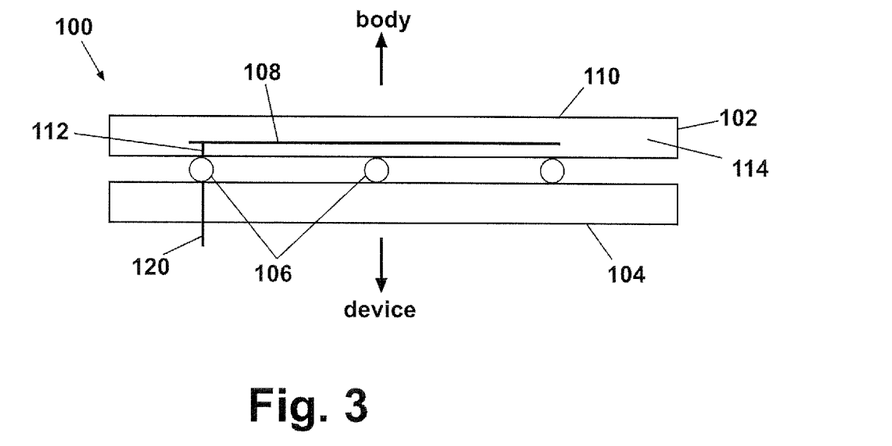
FIG. 3 is a partial cross-sectional block view of an antenna structure for an implantable medical device formed in accordance with one or more embodiments of the present disclosure.

Referring now to FIG. 3, a cross-sectional side view of an antenna structure 100 formed in accordance with one or more embodiments is respectively illustrated. Certain features and aspects of antenna structure 100 are similar to those described above in connection with antenna 28, and shared features and aspects will not be redundantly described in the context of antenna structure 100. Antenna structure 100 includes a biocompatible antenna portion 102 and a high dielectric portion 104. In one or more embodiments, biocompatible antenna portion 102 and high dielectric portion 104 are adhered, joined, bonded, soldered or otherwise connected together by connection points 106 (e.g., by soldering or other adhesive materials, such as a conductive polymer), where connection points 106 further provide an electrical connection between biocompatible antenna portion 102 and high dielectric portion 104.

In one or more embodiments, biocompatible antenna portion 102 is derived from a plurality of layers of material including a layer of biocompatible conductive material that forms antenna 108 and a biocompatible surface layer 110. The biocompatible surface layer 110 is positioned as the outermost layer of the antenna structure serving as an interface for the antenna structure 100 to the surrounding environment (i.e., the body in which the IMD is implanted). Different types of biocompatible materials can be selected based on the intended use of antenna structure 100 and IMD 10 and the intended surrounding environment. For example, outermost layer 105 may comprise inorganic materials, such as Alumina ($Al_2O_3$), zirconium oxide ($ZrO_2$), mixtures thereof, or bonelike systems [hydroxyapatite-$Ca_5(POH)(PO_4)_3$], organic materials, such as silicone and its derivatives, and other traditionally implantable biocompatible materials. In some embodiments, the body side biocompatible antenna portion 102 may include electrical connections 112 and routing circuitry that provide a connection between antenna 108 and other components, such as to IMD circuitry components through a electrical path through connection point 106 and high dielectric portion 104.

In one or more embodiments, antenna 108 may further be embedded within one or more dielectric layers 114 in biocompatible antenna portion 102. Dielectric layers 114 may be selected to be biocompatible, thereby possessing an effective lower dielectric associated with biocompatible materials. For instance, Alumina ($Al_2O_3$) has a dielectric constant k=9. In some embodiments, a plurality of dielectric layers 114 may be provided having respective lower dielectric constants that gradually change in value with each dielectric layer 114 moving away from antenna 108 to values more closely matching the dielectric constant of the environment (e.g., body tissue) surrounding the antenna structure 100, as further illustrated in the cross-sectional illustration of antenna structure 100 of FIG. 4. In this manner, dielectric layers 114 may provide a matching gradient between antenna 108 and the surrounding environment to mitigate energy reflection effects at the transition from the antenna structure 100 to the surrounding environment. The change in dielectric constants in the various dielectric layers 114 can be achieved by incorporating materials that are cofireable, compatible and possess dielectric constants that differ from the other of the dielectric layers 114. In conventional antenna structures possessing abrupt transitions and differences in dielectric constants at the boundary between the antenna structures and the surrounding environment, there can be large energy reflection effects. Such effects are reduced by the matching gradient provided by the dielectric layers 114, where a gradual change in dielectric values between the various dielectric layers 114 may further help to mitigate energy reflection effects between dielectric layers 114.

In one or more embodiments, various biocompatible layers formed in the biocompatible antenna portion 102 may comprise polymers that are loaded with high dielectric constant powders so as to produce a structure for the biocompatible antenna portion 102 that contains a graded dielectric constant extending from one portion of the biocompatible antenna portion 102 to another portion. For example, powders with different dielectric constants can be loaded on the different polymer layers, different concentrations of powder loading can be performed on the different polymer layers, or the dielectric constant of each polymer layer can otherwise have its powder loading adjusted to produce a structure having a graded dielectric constant from one portion of the biocompatible antenna portion 102 to another portion.

In one or more embodiments, high dielectric portion 104 includes at least one dielectric layer 116 having a high dielectric constant for providing isolation between antenna 108 and IMD 10 or other components in order to allow for miniaturization of antenna structure 100. The high dielectric constant K of each layer is achieved by incorporating cofireable materials having high dielectric constants K, e.g. capacitive materials. In one or more embodiments, high dielectric portion 104 may include an shielding layer 118 formed from a metalized material that provides electromagnetic shielding of device circuitry inside of the hermetically sealed housing 14 to which the antenna structure 100 is attached through a feedthrough via 120. In some embodiments, the shielding layer 118 is positioned as the innermost layer of high dielectric portion 104 and thus antenna structure 100, while it is understood that shielding layer 118 can also be positioned within another intermediate layer of high dielectric portion 104. The high dielectric constant of the dielectric layer(s) 116 isolates antenna 108 from interference and other signal interaction which could otherwise result from the hermetically sealed housing 14 of IMD 10 and its respective components. The higher dielectric values associated with dielectric layer(s) 116 further allow the distance between antenna 108 and shielding layer 118 and/or IMD 10 to be minimized, thereby allowing a reduction in size of antenna structure 100 to be achieved. Depending upon the materials used to form high dielectric portion 104, dielectric constant values can vary anywhere from k=5-6 for the LTCC layer itself to at least 1-2 orders of magnitude higher with the use of capacitive pastes that are LTCC compatible. In addition, a ceramic loaded printed wiring board (PWB) is another embodiment to the LTCC based structure. LTCC materials offer the ability to embed passive components to spatially and functionally tailor the dielectric constant or capacitance to optimize packaging efficiency and/or performance. Since materials with high dielectric constants are typically not biocompatible, high dielectric portion 104 is separated and isolated from potential contact with body environment surrounding IMD 10 by the biocompatible materials used to form biocompatible antenna portion 102.

In one or more embodiments, dielectric layers 114 and 118 may comprise at least one of a ceramic material, a semiconductor material, and/or a thin film dielectric material. In one or more embodiments, the plurality of layers used to form dielectric layers 114 of biocompatible antenna portion 102 may comprise a plurality of layers of high temperature cofire ceramic (HTCC) material, while the dielectric layers 118 formed in high dielectric portion 104 comprise a plurality of layers of low temperature cofire ceramic (LTCC) material. Generally, a LTCC material has a melting point between about 850° C. and 1150° C., while a HTCC material has a melting point between about 1100° C. and 1700° C. In one or more embodiments, antenna 108 is formed from a biocompatible conductive material, such as but not limited to at least one of the following materials: Platinum, Iridium, Platinum-Iridium alloys, Alumina, Silver, Gold, Palladium, Silver-Palladium or mixtures thereof, or Molybdenum and/or Moly-manganese or other suitable materials.

In one or more embodiments, all of the layers of materials forming biocompatible antenna portion 102 may be cofired together to form a monolithic structure. Likewise, all of the layers of materials forming high dielectric portion 104 may be cofired together to form a monolithic structure. Methods for co-firing layers of ceramic materials together to form monolithic structures for use in IMDs are described, for example, in U.S. Pat. Nos. 6,414,835 and 7,164,572, the contents of both of which are hereby incorporated by reference in their entireties. The side edges 122 of the various layers of the antenna structure 100 (i.e., side edges 122 of biocompatible antenna portion 102 and high dielectric portion 104) may then be brazed or otherwise hermetically seal the edges 118 of biocompatible antenna portion 102 and high dielectric portion 104 to a ferrule or body that would enable integration of 100 to the housing 14. Generally, brazing involves melting and flowing a brazing material (e.g., a metal such as gold) around the portions of the desired surfaces to be brazed (e.g., the edges 118 of the layers of antenna structure 100).

In one or more embodiments, the plurality of layers in biocompatible antenna portion 102 include a plurality of layers of HTCC material as dielectric layers 114 having lower dielectric constants that are lower than the effective dielectric constant of high dielectric portion 104, where HTCC dielectric layers 114, antenna 108, biocompatible surface layer 110, electrodes 112, and other routing circuitry are cofired together to form biocompatible antenna portion 102 as a monolithic structure. In some embodiments, the biocompatible antenna portion 102 includes an effective lower dielectric constant that provides a matching gradient between the antenna and the surrounding environment to mitigate energy reflection effects at the transition from the antenna structure to the surrounding environment.

Figure 5:
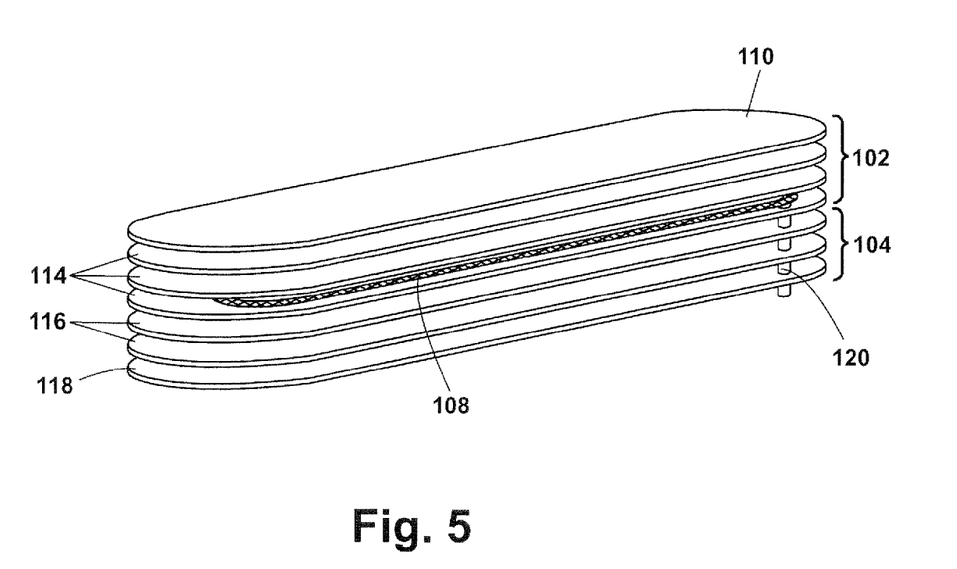
FIG. 5 is a perspective, exploded view of an antenna structure for an implantable medical device formed in accordance with one or more embodiments of the present disclosure.

In one or more embodiments, dielectric layer(s) 116 of high dielectric portion 104 comprise at least one layer of low temperature co-fire ceramic (LTCC) material having a high dielectric constant. In some embodiments, the LTCC dielectric layer(s) 116 may be formed from a high dielectric ceramic powder, such as the powdered filler composites described in U.S. Pat. Nos. 6,107,227 and 6,391,082, the contents of both of which are hereby incorporated by reference in their entireties. LTCC dielectric layer(s) 116, shielding layer 118, connection via 120 and any embedded passive components (not shown) are cofired together to form high dielectric portion 104 as a monolithic structure. High dielectric portion 104 and biocompatible antenna portion 102 may then be bonded together as described herein. Alternatively, high dielectric portion 104 and biocompatible antenna portion 102 may be formed as single bilayer substrate incorporating both HTCC and LTCC technologies in which high dielectric portion 104 and biocompatible antenna portion 102 are cofired together into a single bilayer substrate, as illustrated in FIGS. 5 and 6.

In one or more embodiments, the various layers used to form antenna structure 100 may be formed using any material layer deposition technique known in the art, including but not limited to depositing, spraying, screening, dipping, plating, etc. In some embodiments, molecular beam epitaxy (MBE), atomic layer deposition (ALD) or other thin film, vacuum deposited processes may be used to deposit the various layers building them on top of one another, such that ALD allows thin materials with high dielectric constants to be used in forming substrate dielectric layers 116 and thin materials with low dielectric constants to be used in forming dielectric layers 114, thereby achieving size reduction and miniaturization of overall antenna structure 100 while still improving performing of antenna structure 100. The metal layers can be stacked to form a stacked plate capacitor structure to increase the dielectric constant of the area surrounding the antenna 108.

Figure 4:
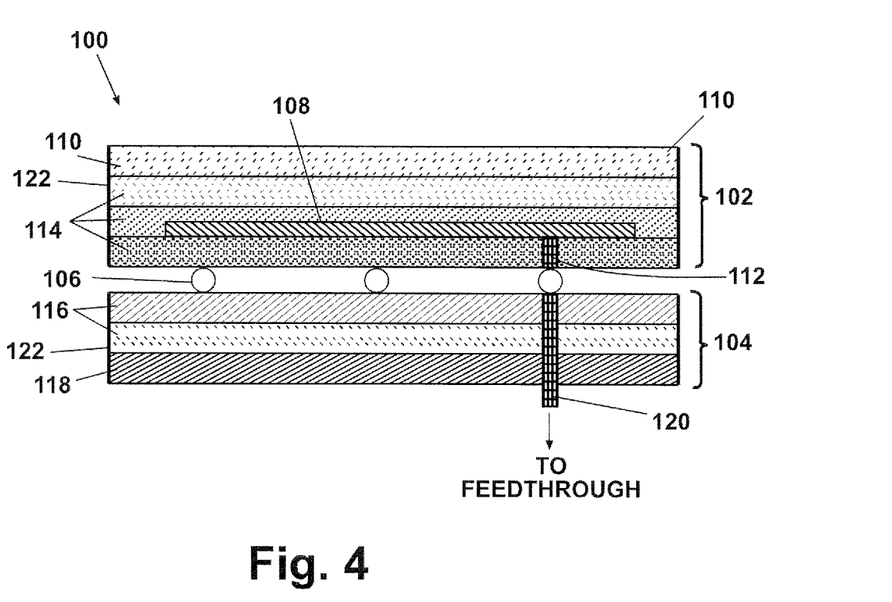
FIG. 4 is a cross-sectional side view of the antenna structure of FIG. 3 formed in accordance with one or more embodiments of the present disclosure.
Figure 6:
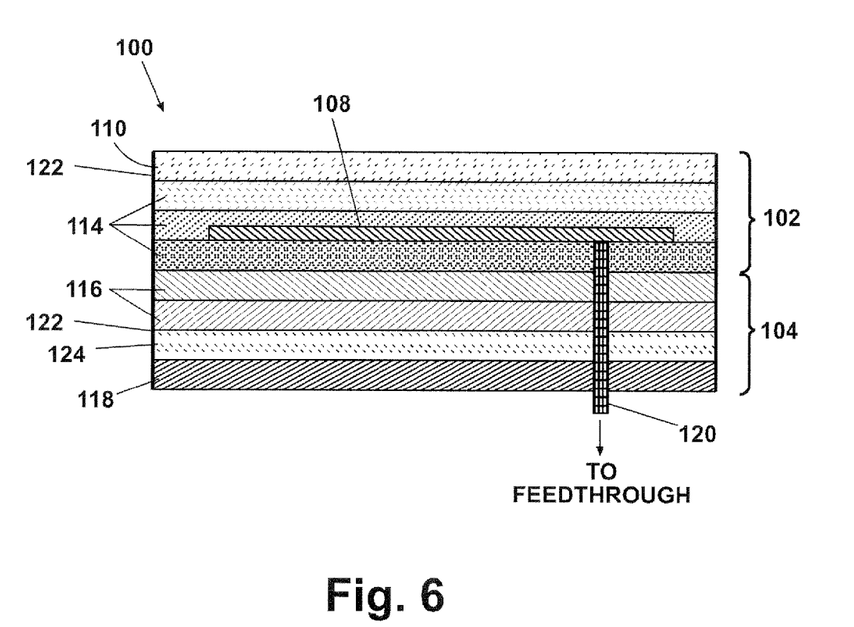
FIG. 6 is a cross-sectional side view of the antenna structure of FIG. 5 formed in accordance with one or more embodiments of the present disclosure.

In one or more embodiments, after the various layers of antenna structure 100 and formed or otherwise deposited with respect to one another, the various layers may be cofired together into separate monolithic biocompatible low dielectric constant HTCC layers 102 and monolithic higher dielectric constant capacitance LTCC layers 104, as illustrated in FIG. 4, or cofired together into a single monolothic bilayer substrate incorporating both HTCC and LTCC technologies, as illustrated in FIG. 6. A feedthrough via 120 extends through monolithic antenna structure 100 and may be used to connect antenna 108 to housing 14, such as through a feedthrough.

In one or more embodiments, the plurality of different individual discrete layers or sheets of materials (or segments of tape) that comprise biocompatible antenna portion 102 and high dielectric portion 104 may be printed with a metalized paste and other circuit patterns, stacked on each other, laminated together and subjected to a predetermined temperature and pressure regimen, and then fired at an elevated temperature(s) during which the majority of binder material(s) (present in the ceramic) and solvent(s) (present in the metalized paste) vaporizes and/or is incinerated while the remaining material fuses or sinters. The number of dielectric layers 114 and 116 may be variably selected based on the desired antenna characteristics. In some embodiments, the materials suitable for use as cofireable conductors for forming the antenna 108 are the biocompatible metal materials described herein or other materials suitable for the metalized paste. In one or more embodiments, the stacked laminates are then cofired together at temperatures between about 850° C. and 1150° C. for LTCC materials and between about 1100° C. and 1700° C. for HTCC materials.

In one or more embodiments in which dielectric layers 114 and 116 include a plurality of planar ceramic layers, each ceramic layer may be shaped in a green state to have a desired layer thickness. In general, the formation of planar ceramic layers starts with a ceramic slurry formed by mixing a ceramic particulate, a thermoplastic polymer and solvents. This slurry is spread into ceramic sheets of predetermined thickness, from which the solvents are volitized, leaving self-supporting flexible green sheets. Holes in certain dielectric layers 114 and 116 that will be filled with conductive material to form vias 112 and 120 are made, using any conventional technique, such as drilling, punching, laser cutting, etc., through the green sheets from which the ceramic layers 104 and 112 are formed. The materials suitable for use as cofireable ceramics include alumina ($Al_2O_3$), aluminum nitride, beryllium oxide, Silica ($SiO_2$), Zirconia ($ZrO_2$), glass-ceramic materials, glass suspended in an organic (polymer) binder, or mixtures thereof.

Furthermore, an electromagnetic bandgap layer 124 may be positioned between antenna 108 and shielding layer 118 (i.e., ground plane), as illustrated in the cross-sectional side view of antenna structure 100 in FIG. 6. Typically, when a radiating antenna element is placed above and in parallel with a ground plane, the field radiated by the antenna element and the field reflected by the ground plane are 180° out of phase due to the reflection coefficient presented by the ground plane short circuit. As a result, when the separation distance between the antenna element and the ground plane is reduced, the total antenna radiated fields tend to zero as the field radiated from the antenna element and its ground plane reflection will tend to completely cancel each other. The electromagnetic bandgap layer 124 prevents this reduction in antenna radiation efficiency by introducing a ground perturbation known as an electromagnetic bandgap, or high impedance surface, between antenna 108 and ground plane shielding layer 118. The electromagnetic bandgap layer 124 prevents or minimizes a reduction in antenna radiation efficiency from occurring as a result of the close proximity of the antenna 108 to the ground plane 118. In one aspect, the electromagnetic bandgap layer 124 at resonance appears as an open circuit with a reflection coefficient in phase with the incident field. For instance, the electromagnetic bandgap layer 124 will cause the field radiated from antenna 108 and the field radiated by its ground plane image to be co-directed thus maintaining the same orientation and not canceling each other out. The electromagnetic bandgap layer 124 further provides a high electromagnetic surface impedance that allows the antenna 108 to lie directly adjacent to the ground plane 118 without being shorted out. This allows compact antenna designs where radiating elements are confined to limited spaces. Thus, the electromagnetic bandgap layer 124 assists in miniaturization of the device by allowing the distance between antenna 108 and ground plane shielding layer 118 to be reduced to a small distance. In one or more embodiments, electromagnetic bandgap layer 124 may be vacuum deposited on the surface of one of the layers of the antenna structure 100 or adhered via epoxy after ceramic densification in order to minimize material alterations induced by thermal excursion of the firing process.

In one or more embodiments, the electromagnetic bandgap layer 124 may comprise a high impedance ground plane (e.g., artificial perfect magnetic conductor or PMC) that has the property of isolating the radiating elements from nearby electromagnetic surroundings. The high impendence surface of the electromagnetic bandgap layer 124 further provides the benefit of directing radiated energy away from ground plane shielding layer 118 and improves the antenna radiated front-to-back ratio resulting in improved antenna efficiency. In one or more embodiments, the electromagnetic bandgap layer 124 is made of is made of a periodic structure, such as a plurality of discrete metal areas or a plurality of periodic lattice cells that are connected electrically to neighboring lattice cells, where such an interconnected bandgap structure topology conducts DC currents but not AC currents within a forbidden band. In one or more embodiments, the physical geometry the electromagnetic bandgap layer 124 may comprise a metal sheet, textured with a 2D lattice of resonant elements which act as a 2D filter to prevent the propagation of electric currents, such as described in the paper, "A High Impedance Ground Plane Applied to a Cellphone Handset Geometry," by Sievenpiper et al., IEEE MTT Vol. 49 No. 7 July 2001 Pg 1262-1265, the contents of which are hereby incorporated by reference in its entirety.

In one or more embodiments, the electromagnetic bandgap layer 124 may comprise a reactive impedance substrate. PMC surfaces are usually constructed from resonant structures operating at resonance. By utilizing a reactive impedance substrate design, the adverse effects of the antenna interaction with the substrate are minimized such as the mutual coupling between the antenna 108 and its image. The electromagnetic bandgap layer 124 can be engineered to exhibit normalized substrate impedance (image impedance) that could compensate for the stored energy in the source itself (antenna 108). If the antenna 108 shows a capacitive load and its image can store magnetic energy, a resonance can be achieved at a frequency much lower than the resonant frequency of the antenna 108 in free space. An example of a reactive impedance substrate is set forth in the paper, "Antenna Miniaturization and Bandwidth Enhancement using a Reactive Impedance Substrate," by Mosallaei et al, IEEE APS vol. 52 No. 9 September 2004 pg 2403-2414, the contents of which are hereby incorporated by reference in its entirety.

Figure 7:
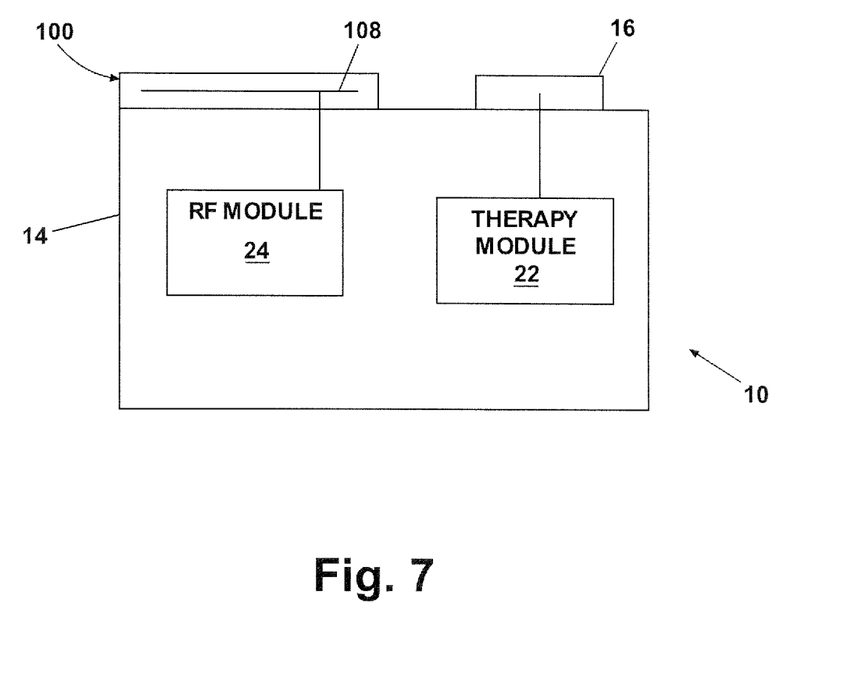
FIG. 7 is a schematic block diagram illustration of an antenna structure connected to an implantable medical device in accordance with one or more embodiments of the present disclosure.

In one or more embodiments, after the antenna structure 100 has been formed as a cofired monolithic structure (or multiple monolithic structures that are interconnected), the brazed side edges 122 of the various layers of the antenna structure 100 along with the outermost biocompatible layer 110 of antenna structure 100 provide a hermetic seal for antenna structure 100 so that it can be connected directly to housing 14, as illustrated in FIG. 7, without requiring a header assembly to enclose and seal the antenna conductor 106 as typically required with conventional far field telemetry antennas for IMDs. Antenna structure 100 may be coupled to housing 14 using brazing, glassing, diffusion bonding or other suitable bonding techniques that will provide a hermetic seal, as known to those skilled in the art. The antenna structure 100 thus reduces the overall volume and physical dimension required for antenna conductor 106 for adequate radiation. In some embodiments, a header block 16 having reduced dimensions may still be utilized for connecting external leads to therapy module 16.

According to one or more embodiments, the use of a cofiring technique to form a monolithic antenna structure 100 including an embedded antenna 108 allows for the manufacture of low-cost, miniaturized, hermetically sealed antenna structures 100 suitable for implantation within tissue and/or in direct or indirect contact with diverse body fluids. Further, by using cofired technologies to form high dielectric portion 104 and biocompatible antenna portion 102, component miniaturization advances can be achieved to significantly reduce the size of the antenna structure used for IMD wireless communications. The use of a cofired multi-layer ceramic antenna structure 100 comprised of cofired materials provide for reduced antenna volume, increased device density and functionality, and the ability to provide embedded antenna functionality, all in a hermetically-sealed monolithic antenna structure 100. For example, in one embodiment, a multi-layer ceramic antenna structure 100 having structural dimensions of 50 mm×12.5 mm×1.0 mm can be produced, while in another embodiment, a multi-layer ceramic antenna structure 100 having structural dimensions of 20 mm×5 mm×0.4 mm can be produced.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A multi-layer antenna for an implantable medical device ("IMD"), comprising:
  a biocompatible antenna portion including:
    an antenna formed from a biocompatible conductive material, and
    at least one layer of biocompatible dielectric material; and
  a high dielectric portion including:
    a ground plane, and
    at least one high dielectric substrate having a high dielectric constant positioned between the antenna and the ground plane,
  wherein the at least one layer of biocompatible dielectric material in the biocompatable antenna portion includes a lower dielectric constant than the at least one high dielectric substrate in the high dielectric portion.

2. The multi-layer antenna of claim 1, wherein the at least one high dielectric substrate is formed from a high dielectric ceramic material.

3. The multi-layer antenna of claim 2, wherein the at least one high dielectric substrate comprises a low temperature co-fire ceramic (LTCC) material having a melting point between about 850 co and 1150 co and a cofireable paste having a high dielectric constant.

4. The multi-layer antenna of claim 1, wherein the high dielectric portion is physically and electrically connected to the biocompatible antenna portion.

5. The multi-layer antenna of claim 4, wherein the high dielectric portion is joined to the biocompatible portion through at least one bond that comprises one of a solder, a conductive epoxy and a metallurgical-based bond.

6. The multi-layer antenna of claim 1, wherein the biocompatible portion and high dielectric portion are separately formed monolithic structures that are connected together.

7. The multi-layer antenna of claim 3, wherein the at least one layer of biocompatible dielectric material in the biocompatible antenna portion comprises a high temperature co-fire ceramic (HTCC) material having a melting point between about 1100 co and 1700 co, further wherein the biocompatible antenna portion and the high dielectric portion are joined together to form a single bilayer monolithic antenna structure having a lower dielectric HTCC biocompatible antenna portion and a LTCC high dielectric portion.

8. The multi-layer antenna of claim 7, wherein the HTCC biocompatible antenna portion and the LTCC high dielectric portion are joined together by an adhering material.

9. The multi-layer antenna of claim 7, wherein the HTCC biocompatible antenna portion and the LTCC high dielectric portion are cofired together.

10. The multi-layer antenna of claim 1, wherein the ground plane in the high dielectric portion further provides a shielding layer for providing electromagnetic shielding between the antenna and the IMD to which the antenna is connected.

11. The multi-layer antenna of claim 1, wherein the high dielectric portion further includes a layer of electromagnetic bandgap material.

* * * * *